(12) United States Patent
Chanduszko et al.

(10) Patent No.: US 12,427,294 B2
(45) Date of Patent: Sep. 30, 2025

(54) IMPLANTABLE PORTS, IMPLANTABLE PORT-DETECTING DEVICES, AND METHODS THEREOF

(71) Applicant: Bard Peripheral Vascular, Inc., Franklin Lakes, NJ (US)

(72) Inventors: Andrzej J. Chanduszko, Chandler, AZ (US); Peng Zheng, Chandler, AZ (US); Sima Jalaleddine, Phoenix, AZ (US); Joceline D. Cooks, El Mirage, AZ (US); Jeremy B. Cox, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1214 days.

(21) Appl. No.: 17/260,204

(22) PCT Filed: Jul. 12, 2019

(86) PCT No.: PCT/US2019/041708
§ 371 (c)(1),
(2) Date: Jan. 13, 2021

(87) PCT Pub. No.: WO2020/014674
PCT Pub. Date: Jan. 16, 2020

(65) Prior Publication Data
US 2021/0268251 A1 Sep. 2, 2021

Related U.S. Application Data (60) Provisional application No. 62/697,793, filed on Jul. 13, 2018.

(51) Int. Cl.
*A61M 39/02* (2006.01)
*A61M 39/00* (2006.01)
*A61M 39/04* (2006.01)

(52) U.S. Cl.
CPC ........ *A61M 39/0208* (2013.01); *A61M 39/04* (2013.01); *A61M 2039/0009* (2013.01); *A61M 2039/0238* (2013.01)

(58) Field of Classification Search
CPC .............. A61M 39/0208; A61M 39/04; A61M 2039/0009; A61M 2039/0238;
(Continued)

(56) References Cited

U.S. PATENT DOCUMENTS 4,222,374 A   9/1980 Sampson et al.
4,784,646 A   11/1988 Feingold
(Continued)

FOREIGN PATENT DOCUMENTS

WO   2011034529 A1   3/2011
WO   2014/031763 A2   2/2014
(Continued)

OTHER PUBLICATIONS

PCT/US2019/041708 filed Jul. 12, 2019 International Search Report and Written Opinion dated Nov. 12, 2019.
(Continued)

*Primary Examiner* — Theodore J Stigell
(74) *Attorney, Agent, or Firm* — Rutan & Tucker LLP (57) ABSTRACT

Disclosed herein is an implantable port and an implantable port-detecting device ("IPDD"). The implantable port includes a housing and a septum over a portion of the housing. At least one of the housing or the septum incorporates a contrast agent for locating the septum of the implantable port when the implantable port is implanted in a patient. The IPDD includes a light source, a light detector, and a display configured to display a presence of the implantable port. The light source is configured to emit light in a near-infrared ("NIR") range of wavelengths as incident light for absorption by the contrast agent. The light detector
(Continued)

is configured to detect light in the NIR range of wavelengths including luminescent light emitted by the contrast agent. The display is configured to display a presence of the implantable port when the luminescent light from the contrast agent is detected by the light detector.

23 Claims, 10 Drawing Sheets

(58) Field of Classification Search
CPC ..... A61B 5/0071; A61B 5/0082; A61B 5/684; A61B 90/30; A61B 90/361; A61B 2090/373; A61B 2090/3937; A61B 2090/3941; A61B 2576/00; A61B 5/061; A61B 90/90
See application file for complete search history.

(56) References Cited

U.S. PATENT DOCUMENTS

| | | |
|---|---|---|
| 4,804,054 A | 2/1989 | Howson et al. |
| 5,171,228 A | 12/1992 | McDonald |
| 5,201,715 A | 4/1993 | Masters |
| 5,360,407 A | 11/1994 | Leonard et al. |
| 5,375,596 A | 12/1994 | Twiss et al. |
| 5,423,334 A | 6/1995 | Jordan |
| 5,620,419 A | 4/1997 | Lui et al. |
| 5,676,146 A | 10/1997 | Scarborough |
| 5,758,667 A | 6/1998 | Slettenmark |
| 5,944,023 A | 8/1999 | Johnson et al. |
| 6,009,878 A | 1/2000 | Weijand et al. |
| 6,287,293 B1 | 9/2001 | Jones et al. |
| 6,755,199 B2 | 6/2004 | Rehder et al. |
| 6,962,580 B2 | 11/2005 | Adams et al. |
| 7,191,011 B2 | 3/2007 | Cantlon |
| 7,255,682 B1 | 8/2007 | Bartol, Jr. et al. |
| 7,334,582 B2 | 2/2008 | Bertrand et al. |
| 7,637,897 B2 | 12/2009 | Ginggen |
| 7,727,143 B2 | 6/2010 | Birk et al. |
| 7,775,215 B2 | 8/2010 | Hassler, Jr. et al. |
| 7,794,451 B1 | 9/2010 | Chuter et al. |
| 7,806,122 B2 | 10/2010 | Hoendervoogt et al. |
| 7,878,207 B2 | 2/2011 | Goetz et al. |
| 7,942,863 B2 | 5/2011 | Kalpin et al. |
| 8,015,977 B2 | 9/2011 | Bertrand et al. |
| 8,075,536 B2 | 12/2011 | Gray et al. |
| 8,171,938 B2 | 5/2012 | Bengtson |
| 8,186,358 B2 | 5/2012 | Crivelli et al. |
| 8,192,398 B2 | 6/2012 | Hoendervoogt et al. |
| 8,257,325 B2 | 9/2012 | Schweikert et al. |
| 8,475,407 B2 | 7/2013 | Kalpin et al. |
| 8,483,802 B2 | 7/2013 | Kalpin et al. |
| 8,534,293 B2 | 9/2013 | Bzostek et al. |
| 8,550,981 B2 | 10/2013 | Woodruff et al. |
| 8,573,228 B2 | 11/2013 | Kalpin |
| 8,622,978 B2 | 1/2014 | Bertrand et al. |
| 8,630,695 B2 | 1/2014 | Negre et al. |
| 8,721,605 B2 | 5/2014 | Brandt et al. |
| 8,805,478 B2 | 8/2014 | Powers et al. |
| 8,882,655 B2 | 11/2014 | Nitka et al. |
| 8,905,916 B2 | 12/2014 | Jacobs et al. |
| 9,060,840 B2 | 6/2015 | Woodruff et al. |
| 9,125,718 B2 | 9/2015 | Augarten |
| 9,526,441 B2 | 12/2016 | Wilhelm et al. |
| 9,556,308 B1* | 1/2017 | Waymouth ........... C07D 409/12 |
| 9,603,997 B2 | 3/2017 | Humayun et al. |
| 9,636,210 B2 | 5/2017 | Hristov et al. |
| 9,700,408 B1 | 7/2017 | Sataloff |
| 9,814,566 B1 | 11/2017 | Cree |
| 9,884,150 B2 | 2/2018 | Jho et al. |
| 9,901,687 B2 | 2/2018 | Meng et al. |
| 10,010,404 B2 | 7/2018 | McClellan |
| 10,022,094 B2 | 7/2018 | Kerr et al. |
| 10,143,827 B2 | 12/2018 | Bittenson |
| 10,188,844 B2 | 1/2019 | Patisteas et al. |
| 10,238,850 B2 | 3/2019 | Maniar et al. |
| 2004/0064030 A1 | 4/2004 | Forsell |
| 2006/0240489 A1* | 10/2006 | Wei ........................ C07C 333/16 548/304.1 |
| 2007/0078391 A1 | 4/2007 | Wortley et al. |
| 2007/0233017 A1 | 10/2007 | Zinn et al. |
| 2008/0051722 A1 | 2/2008 | Ellsmere et al. |
| 2009/0105688 A1 | 4/2009 | McIntyre et al. |
| 2010/0204564 A1 | 8/2010 | Dobson et al. |
| 2011/0196195 A1 | 8/2011 | Raven et al. |
| 2011/0264104 A1 | 10/2011 | Naoum |
| 2011/0295104 A1 | 12/2011 | Teitelbaum et al. |
| 2012/0018764 A1 | 1/2012 | Choi et al. |
| 2012/0289819 A1 | 11/2012 | Snow |
| 2013/0172733 A1* | 7/2013 | Maniar ..................... A61B 6/12 600/424 |
| 2014/0046191 A1 | 2/2014 | Anker et al. |
| 2014/0199381 A1 | 7/2014 | Mng et al. |
| 2014/0228765 A1 | 8/2014 | Burke et al. |
| 2015/0087969 A1 | 3/2015 | Shekhar et al. |
| 2015/0100032 A1 | 4/2015 | Finberg et al. |
| 2015/0148665 A1* | 5/2015 | Sato ................. A61M 39/0208 348/162 |
| 2015/0238118 A1 | 8/2015 | Legassey et al. |
| 2015/0297115 A1 | 10/2015 | Babu |
| 2016/0325111 A1* | 11/2016 | Bourke, Jr. ............. A61P 27/02 |
| 2016/0325112 A1* | 11/2016 | Zweig .................. A61L 31/022 |
| 2017/0182263 A1 | 6/2017 | Geiger |
| 2018/0028746 A1 | 2/2018 | Abrams et al. |
| 2018/0126147 A1 | 5/2018 | Hakim |
| 2018/0336381 A1 | 11/2018 | Homanfar et al. |
| 2019/0029760 A1 | 1/2019 | Nahman et al. |
| 2019/0117883 A1 | 4/2019 | Abrams et al. |

FOREIGN PATENT DOCUMENTS

| | | |
|---|---|---|
| WO | 2018200333 A1 | 11/2018 |
| WO | 2018217633 A1 | 11/2018 |
| WO | 2018221417 A1 | 12/2018 |
| WO | 2020014674 A1 | 1/2020 |

OTHER PUBLICATIONS

Fan, W. et al., "On The Latest Three-Stage Development of Nanomedicines based on Upconversion Nanoparticles," Adv. Mater. 2016, 28, 3987-401.

Li, L., et al., "Biomimetic Surface Engineering of Lanthanide-Doped Upconversion Nanoparticles as Versatile 2 Bioprobes," Angew. Chem. Int. Ed. 2012, 51, 6121-6125.

Maji, S. K., et al., "Upconversion Nanoparticles as a Contrast Agent for Photoacoustic Imaging in Live Mice," Adv. Mater. 2014, 26, 5633-5638.

* cited by examiner

IMPLANTABLE PORTS, IMPLANTABLE PORT-DETECTING DEVICES, AND METHODS THEREOF

PRIORITY

This application is a U.S. national stage application of International Application No. PCT/US2019/041708, which claims the benefit of priority to U.S. Provisional Application No. 62/697,793, filed Jul. 13, 2018, each of which is incorporated by reference in its entirety into this application.

BACKGROUND

Implantable access ports, or simply "ports," such as central venous access ports provide a convenient method to repeatedly deliver a substance to remote areas of the body by way of an attached catheter without utilizing a surgical procedure each time. Ports are implantable within the body and permit the infusion of medicine, parenteral solutions, blood products, or other fluids. Additionally, ports are also used for blood sampling. In common practice, a port is subcutaneously implanted within the body, and a catheter is connected to the port in fluid communication therewith. The catheter is routed to a remote area where a fluid is desired to be delivered or removed. To deliver the fluid, a caregiver locates a septum of the port by palpation of a patient's skin. Port access is accomplished by percutaneously inserting a needle, typically a non-coring needle, through the septum of the port and into a chamber of the port. A fluid containing a drug or some other beneficial substance can then be administered by bolus injection or continuous infusion into the chamber of the port. The fluid then flows through the chamber into the catheter and finally to the remote site where the fluid is desired.

Ports, particularly port septa, can be difficult to find once the ports are implanted under the skin. Accordingly, there is a need to facilitate finding medical devices such as ports and their septa once such medical devices are implanted. Disclosed herein are at least implantable ports, implantable port-detecting devices, and methods thereof.

SUMMARY

Disclosed herein is an implantable port including, in some embodiments, a housing and a septum over the housing. The housing includes a chamber having a major opening to the chamber. The septum is over the major opening of the housing. One or more portions of the implantable port incorporate a contrast agent for locating the septum of the implantable port in vivo by opto-electronic excitation and detection of the contrast agent.

In some embodiments, the septum of the implantable port incorporates the contrast agent.

In some embodiments, the housing of the implantable port incorporates the contrast agent around at least the major opening of the housing.

In some embodiments, the contrast agent includes nanoparticles, quantum dots, one or more fluorescent dyes, or a combination thereof.

In some embodiments, the contrast agent includes up-converting nanoparticles including lanthanide- or actinide-doped transition metals.

In some embodiments, the contrast agent includes core-shell nanoparticles.

In some embodiments, the contrast agent includes gold nanoparticles configured to absorb incident light in an NIR range of wavelengths and emit luminescent light in the NIR range of wavelengths.

In some embodiments, the gold nanoparticles include a capping ligand derived from biotin, methoxy polyethyleneglycol, or citric acid.

In some embodiments, the implantable port including the contrast agent is stable to conditions associated with autoclave-based sterilization up to a temperature of at least 60° C.

In some embodiments, the housing has a structural integrity for mechanically assisted pressurized injections to achieve a desired flow rate of injectant through the implantable port.

Also disclosed herein is a catheter assembly including, in some embodiments, an implantable port, a catheter, and a catheter lock configured to lock the catheter on the implantable port. The implantable port includes a housing, a septum over the housing, and a stem extending from the housing. The housing includes a chamber having a major opening and a minor opening to the chamber. The septum is over the major opening of the housing. The stem includes a stem lumen fluidly connected to the chamber by the minor opening of the housing. One or more portions of the implantable port incorporate a contrast agent for locating the septum of the implantable port in vivo by opto-electronic excitation and detection of the contrast agent. The catheter includes an end portion configured to slide over the stem of the implantable port. The catheter has a catheter lumen in fluid communication with the chamber of the implantable port by way of the stem lumen. The catheter lock is configured to slide over the end portion of the catheter over the stem of the implantable port, thereby locking the catheter on the stem of the implantable port.

In some embodiments, the septum of the implantable port incorporates the contrast agent. Alternatively, the housing of the implantable port incorporates the contrast agent around at least the major opening of the housing.

In some embodiments, the catheter, the catheter lock, or both the catheter and the catheter lock incorporate the contrast agent.

In some embodiments, the contrast agent includes gold nanoparticles configured to absorb incident light in an NIR range of wavelengths and emit luminescent light in the NIR range of wavelengths.

In some embodiments, the gold nanoparticles include a capping ligand derived from biotin, methoxy polyethyleneglycol, or citric acid.

In some embodiments, the implantable port including the contrast agent is stable to conditions associated with autoclave-based sterilization up to a temperature of at least 60° C.

In some embodiments, the housing of the implantable port has a structural integrity for mechanically assisted pressurized injections to achieve a desired flow rate of injectant through the implantable port.

Also disclosed herein is an implantable port-detecting device ("IPDD") including, in some embodiments, a light source, a light detector, and a display configured to display a presence of an implantable port. The light source is configured to emit light of one or more wavelengths in an NIR range of wavelengths as incident light for absorption by a contrast agent incorporated into one or more portions of an implantable port. The light detector is configured to detect light of one or more same or different wavelengths in the NIR range of wavelengths including luminescent light emitted by the contrast agent after the incident light is absorbed by the contrast agent. The display is configured to display a presence of the implantable port when the luminescent light from the contrast agent is detected by the light detector.

In some embodiments, the light detector is an NIR-sensitive camera configured to capture images or video of at least a portion of an environment including the implantable port together with the luminescent light from the contrast agent when the luminescent light is present.

In some embodiments, the display is configured to display the images or the video, thereby providing the presence of the implantable port.

In some embodiments, the IPDD further includes an optical filter over an aperture of the camera configured to cut off wavelengths of interfering light to improve contrast in the images or the video.

In some embodiments, the optical filter is a dichroic filter configured as a bandpass or longpass filter that cuts off wavelengths shorter than about 600 nm.

In some embodiments, the IPDD further includes a battery and converter for charging the battery. The converter is configured to convert AC to DC for charging the battery by a general-purpose AC electric-power supply.

In some embodiments, the IPDD is a handheld device.

Also disclosed herein is an implantable port-detection system including, in some embodiments, an implantable port and an IPDD. The implantable port includes a housing including a chamber having a major opening to the chamber. The septum is over the major opening of the housing. One or more portions of the implantable port incorporate a contrast agent for locating the septum of the implantable port when the implantable port is implanted in a patient. The IPDD includes a light source, a light detector, and a display configured to display a presence of the implantable port. The light source is configured to emit light of one or more wavelengths in an NIR range of wavelengths as incident light for absorption by the contrast agent incorporated into the one or more portions of the implantable port. The light detector is configured to detect light of one or more same or different wavelengths in the NIR range of wavelengths including luminescent light emitted by the contrast agent after the incident light is absorbed by the contrast agent. The display is configured to display a presence of the implantable port when the luminescent light from the contrast agent is detected by the light detector.

In some embodiments, the septum of the implantable port incorporates the contrast agent. Alternatively, the housing of the implantable port incorporates the contrast agent around at least the major opening of the housing.

In some embodiments, the contrast agent includes gold nanoparticles configured to absorb the incident light of the one or more wavelengths in the NIR range of wavelengths and emit the luminescent light of the one or more same or different wavelengths in the NIR range of wavelengths.

In some embodiments, the one or more wavelengths of the incident light correspond to a peak absorption of the gold nanoparticles in the NIR range of wavelengths.

In some embodiments, the gold nanoparticles include a capping ligand derived from biotin, methoxy polyethyleneglycol, or citric acid.

In some embodiments, the light detector is an NIR-sensitive camera configured to capture images or video of at least a portion of a body surface of the patient together with the luminescent light from the gold nanoparticles when the luminescent light is present. The display is configured to display the images or the video, thereby providing the presence of the implanted port in the patient.

In some embodiments, the implantable port-detection system further includes an optical filter between the camera and the patient configured to cut off wavelengths of interfering light to improve contrast in the images or the video. The optical filter is a dichroic filter configured as a bandpass or longpass filter that cuts off wavelengths shorter than about 600 nm.

In some embodiments, the implantable port-detection system further includes a battery and a converter for charging the battery. The converter is configured to convert AC to DC for charging the battery by a general-purpose AC electric-power supply.

In some embodiments, the IPDD is a handheld device.

Also disclosed herein is a method of a port-detection system including, in some embodiments, emitting light from a light source of an IPDD as incident light, detecting light with a light detector of the IPDD including luminescent light from an implantable port implanted in a patient, and displaying a presence of the implanted port in the patient. The incident light emitted from the light source of the IPDD is of one or more wavelengths in an NIR range of wavelengths. The luminescent light from the implantable port is luminescent light emitted by a contrast agent incorporated into the implantable port after the incident light is absorbed by the contrast agent. The luminescent light is of one or more same or different wavelengths in the NIR range of wavelengths. Displaying the presence of the implanted port in the patient occurs when the luminescent light from the contrast agent is detected by the light detector.

In some embodiments, a septum of the implantable port incorporates the contrast agent. Alternatively, a housing of the implantable port incorporates the contrast agent around at least a major opening of the housing covered by the septum.

In some embodiments, the method further includes piercing the septum of the implantable port with a non-coring needle to collect a blood sample from a chamber of the implantable port or deliver a therapeutic agent to the chamber of the implantable port.

In some embodiments, the contrast agent includes gold nanoparticles configured to absorb the incident light of the one or more wavelengths in the NIR range of wavelengths and emit the luminescent light of the one or more same or different wavelengths in the NIR range of wavelengths.

In some embodiments, the light detector is an NIR-sensitive camera configured to capture images or video. Displaying the presence of the implanted port in the patient includes displaying the images or the video of at least a portion of a body surface of the patient together with the luminescent light emitted by the contrast agent incorporated into the implantable port when the luminescent light is present.

In some embodiments, the method further includes removing the implantable port implanted in the patient.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Abbreviations, initialisms, acronyms, or the like used herein include near-infrared ("NIR"), implantable port-detecting device ("IPDD"), alternating current ("AC"), direct current ("DC"), charge-coupled device ("CCD"), graphical user interface ("GUI"), and light-emitting diode ("LED").

Unless defined otherwise, all technical and scientific terms used herein have the same meaning as commonly understood by those of ordinary skill in the art.

Ports, particularly port septa, can be difficult to find once the ports are implanted under the skin. Accordingly, there is a need to facilitate finding medical devices such as ports and their septa once such medical devices are implanted. As such, set forth below are various implantable port-detection systems, catheter assemblies including implantable ports, the implantable ports, and implantable port-detecting devices. Methods associated with the foregoing are also set forth below.

Implantable Port-Detection System

Figure 1:
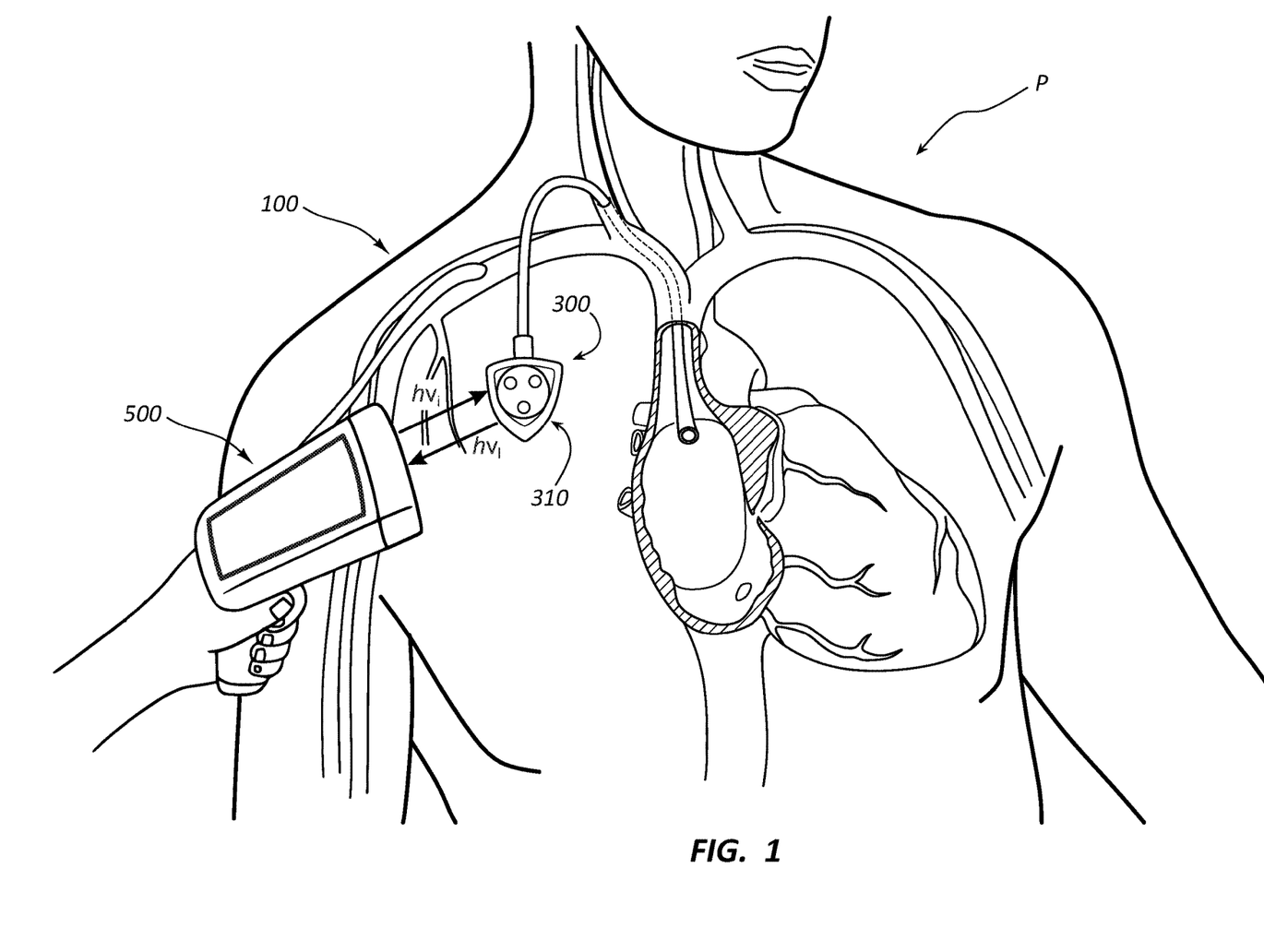
FIG. 1 illustrates an implantable port-detection system being used to find an implantable port implanted in a patient in accordance with some embodiments.
Figure 2:
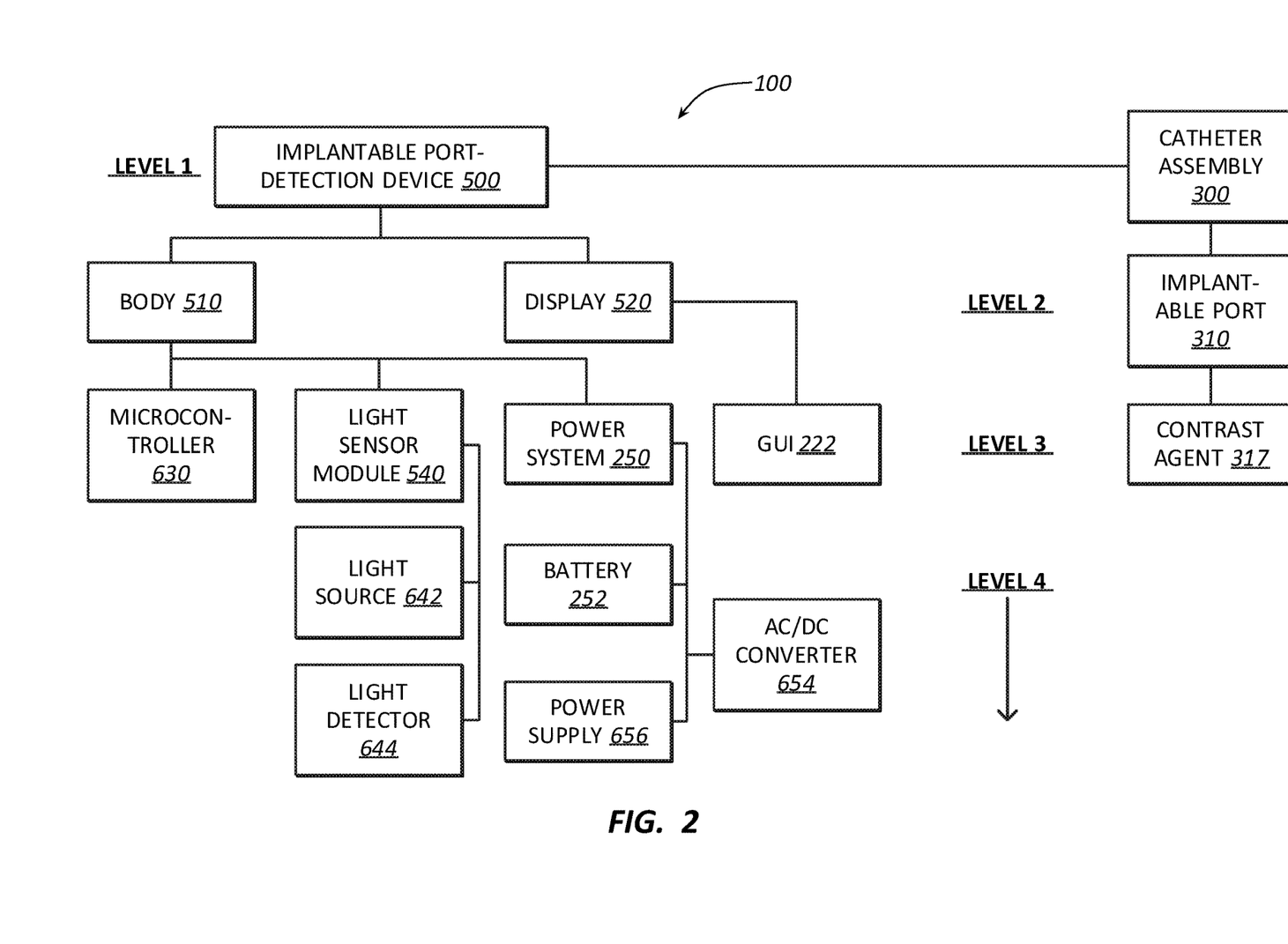
FIG. 2 illustrates a hierarchical view of an implantable port-detection system in accordance with some embodiments.

FIG. 1 illustrates an implantable port-detection system 100 being used to find an implantable port 310 implanted in a patient P in accordance with some embodiments. FIG. 2 illustrates a hierarchical view of the implantable port-detection system 100 in accordance with some embodiments.

As shown, the implantable port-detection system 100 includes, in some embodiments, an IPDD 500 and a catheter assembly 300 including the implantable port 310. As set forth in more detail below, one or more portions of the implantable port 310 incorporate a contrast agent 317 (see FIGS. 3A-3C) for locating a septum 314 (see FIGS. 3A-3C) of the implantable port 310 when the implantable port 310 is implanted in the patient P. The IPDD 500 includes a light source 642 (see also FIG. 6) configured to emit light of one or more wavelengths in an NIR range of wavelengths as incident light $hv_i$ for absorption by the contrast agent 317 incorporated into the one or more portions of the implantable port 310. The incident light is of one or more wavelengths at or near a peak absorbance of the contrast agent 317. The IPDD 500 also includes a light detector 644 (see FIG. 6) configured to detect light of one or more same or different wavelengths in the NIR range of wavelengths including luminescent light $hv_l$ emitted by the contrast agent 317 after the incident light is absorbed by the contrast agent 317. The IPDD 500 also includes a display 520 (see also FIG. 5) configured to display a presence of the implantable port 310 when the luminescent light from the contrast agent 317 is detected by the light detector 644.

Catheter Assemblies Including Implantable Ports

Figure 3A:
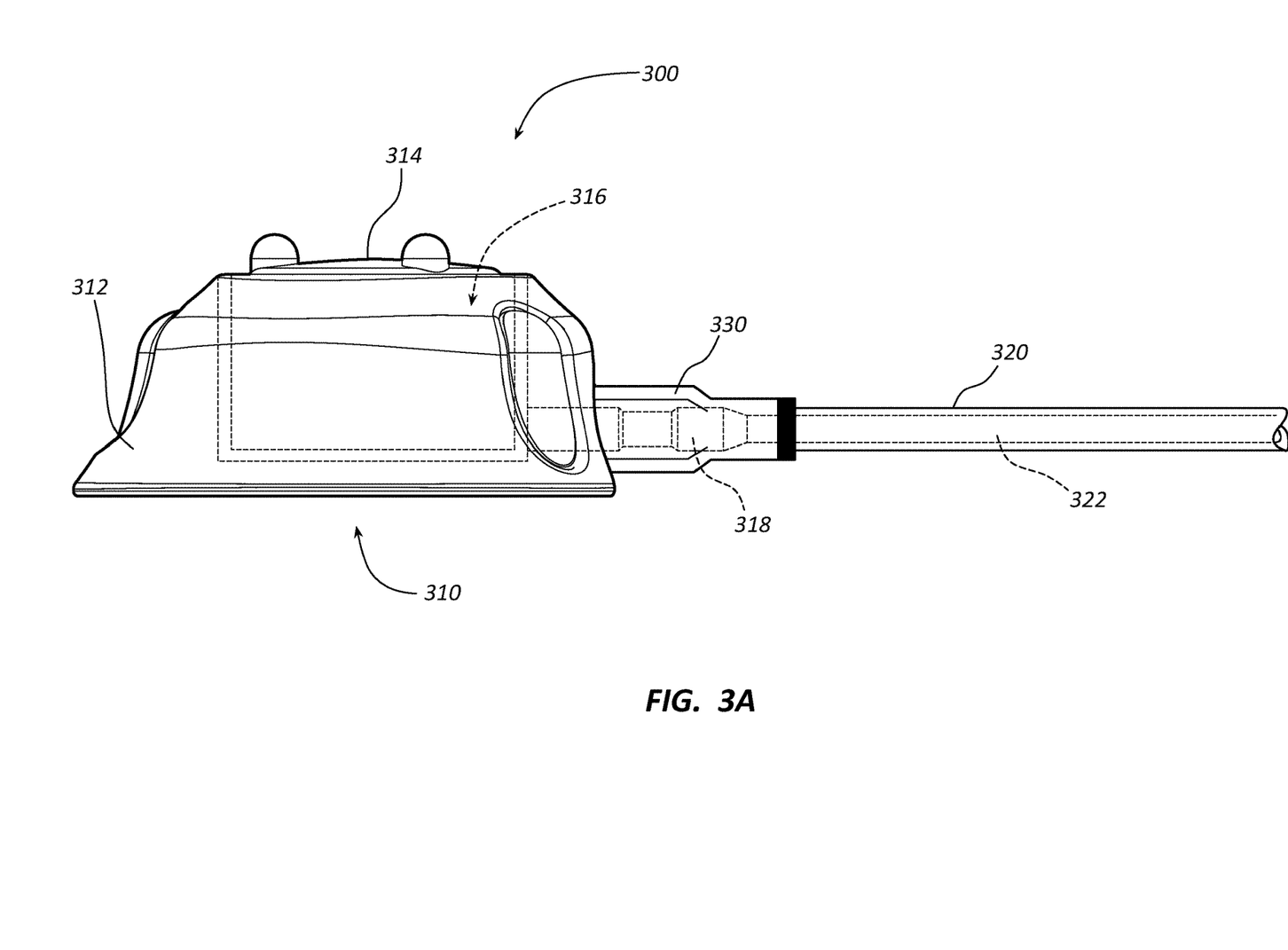
FIG. 3A illustrates a side view of a catheter assembly including an implantable port in accordance with some embodiments.
Figure 3B:
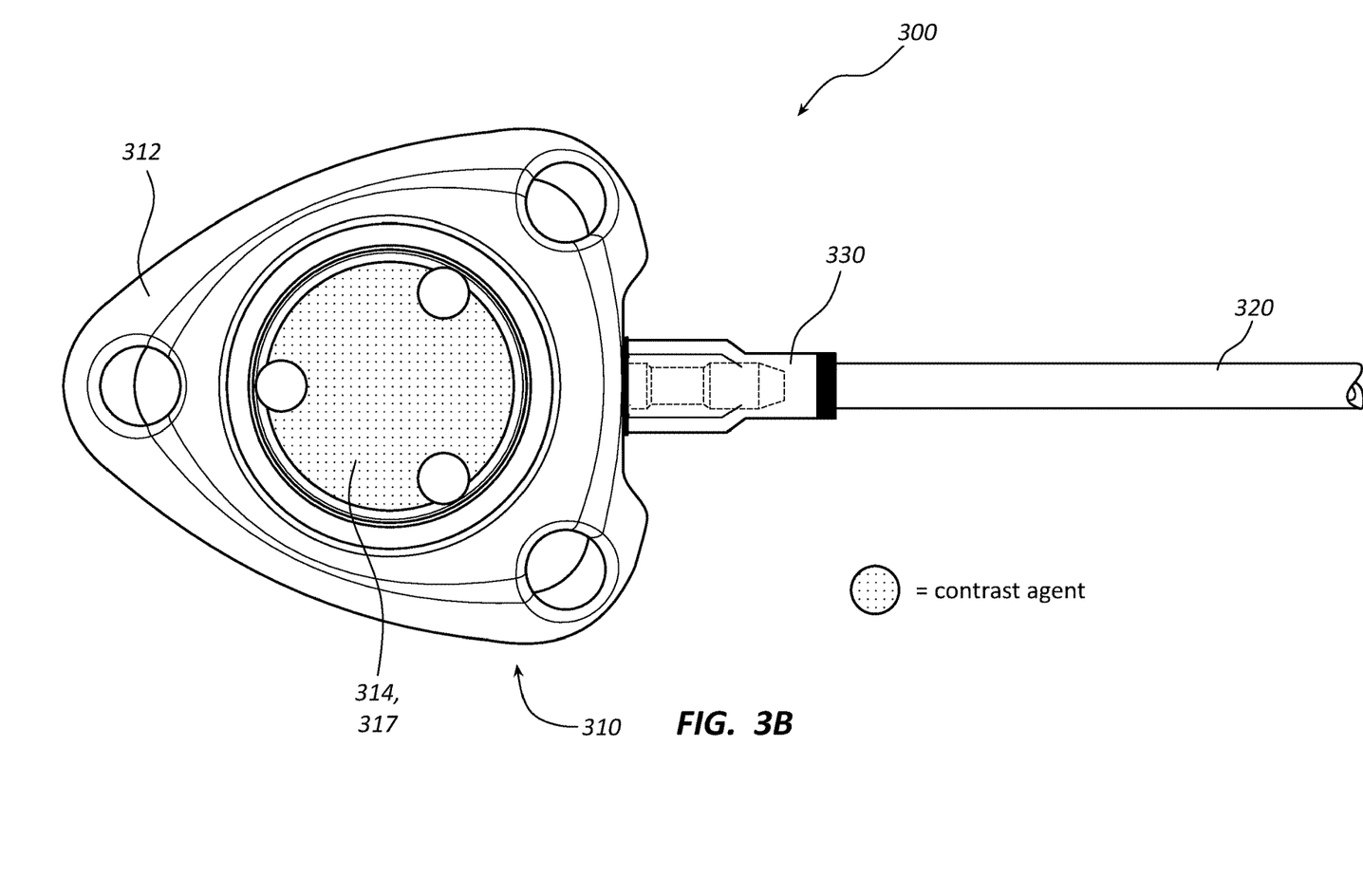
FIG. 3B illustrates a top view of a catheter assembly including an implantable port in accordance with some embodiments.
Figure 3C:
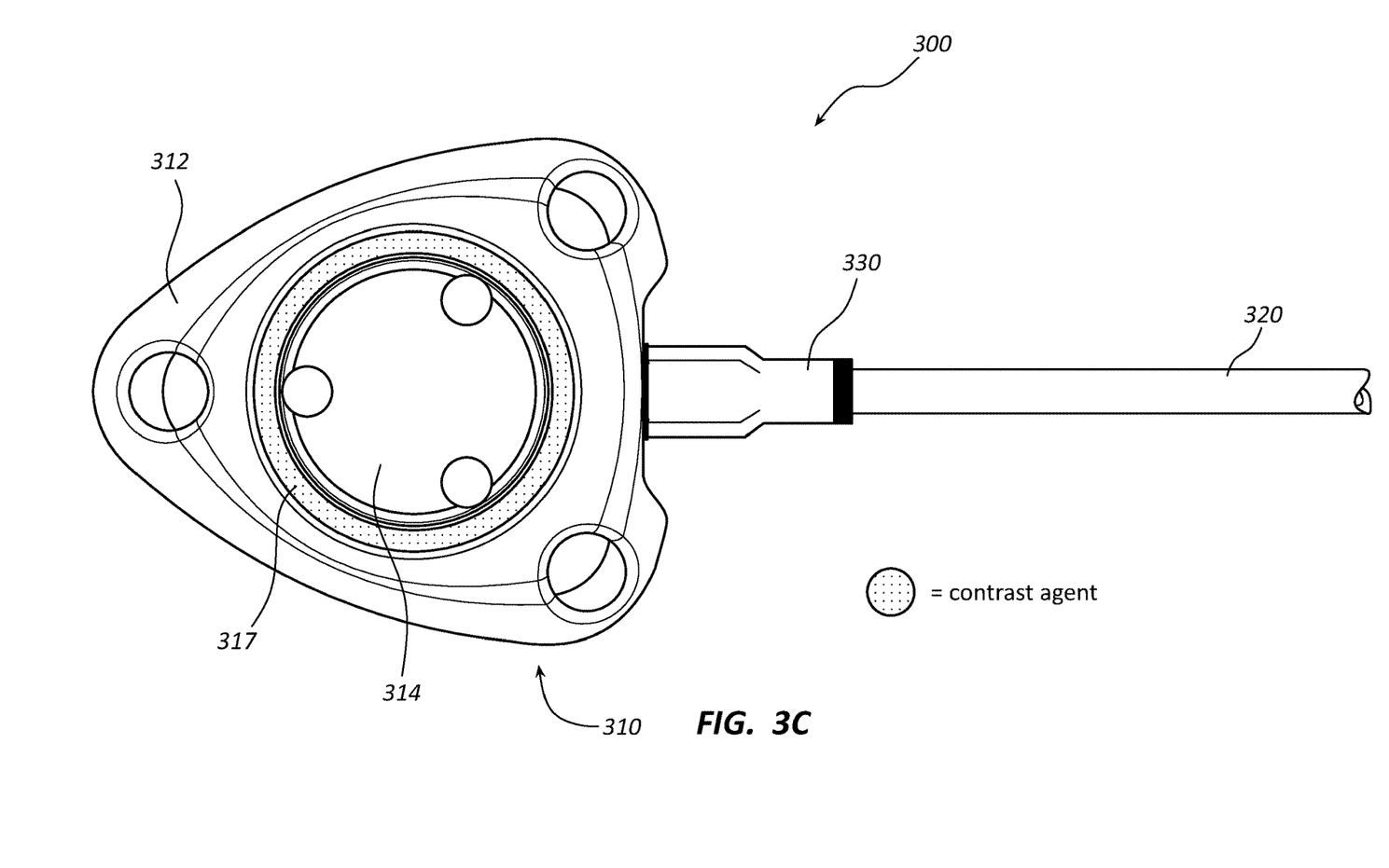
FIG. 3C illustrates top view of a catheter assembly including an implantable port in accordance with some embodiments.

FIG. 3A illustrates a side view of the catheter assembly 300 including the implantable port 310 in accordance with some embodiments. FIGS. 3B and 3C illustrate top views of the catheter assembly 300 including the implantable port 310 in accordance with some embodiments.

As shown, the catheter assembly 300 includes, in some embodiments, the implantable port 310, a catheter 320, and a catheter lock 330 configured to lock the catheter 320 on the implantable port 310. As set forth in more detail below, the implantable port 310 includes a housing 312 and a hollow stem 318 extending from the housing 312. The catheter 320 includes an end portion configured to slide over the stem 318 of the implantable port 310. The catheter 320 has a catheter lumen 322 in fluid communication with a chamber 316 of the implantable port 310 by way of a stem lumen (not shown) of the stem 318. The catheter lock 330 is configured to slide over the end portion of the catheter 320 over the stem 318 of the implantable port 310, thereby locking the catheter 320 on the stem 318 of the implantable port 310.

While one or more portions of the implantable port 310 incorporate the contrast agent 317 for locating the septum 314 of the implantable port 310, the catheter 320, the catheter lock 330, or both the catheter 320 and the catheter lock 330 can incorporate a same or different contrast agent. Incorporation of such a contrast agent into the catheter 320 or the catheter lock 330 effectively expands an area of the patient P over which contrast agent is distributed. This can facilitate searching for an implanted port (e.g., the implantable port 310) in certain anatomies (e.g., obese patients). For example, once a catheter such as the (e.g., the catheter 320) incorporating a contrast agent (e.g., the contrast agent 317) is found, a clinician can follow the catheter by way of its luminescence to the implanted port. The clinician can then identify a septum of the implanted port by the luminescence of the contrast agent in the one or more portions of the implanted port.

Implantable Ports

Again, FIG. 3A illustrates a side view of the catheter assembly 300 including the implantable port 310 in accordance with some embodiments. FIGS. 3B and 3C illustrate top views of the catheter assembly 300 including the implantable port 310 in accordance with some embodiments in which the contrast agent 317 is incorporated differently.

As shown, the implantable port 310 includes, in some embodiments, the housing 312, the septum 314 over at least a portion of the housing 312, and the stem 318 extending from the housing 312. The housing 312 can have a structural integrity for mechanically assisted pressurized injections to achieve a desired flow rate of injectant through the implantable port 310. The housing 312 includes the chamber 316 for such injections, the housing 312 having a major opening to the chamber 316 and a minor opening to the chamber 316. The septum 314 is over the major opening of the housing 312, thereby closing or sealing off the chamber 316 and requiring a needle for access to the chamber 316. The stem 318 includes a stem lumen (not shown) fluidly connected to the chamber 316 by the minor opening of the housing 312.

Figure 5:
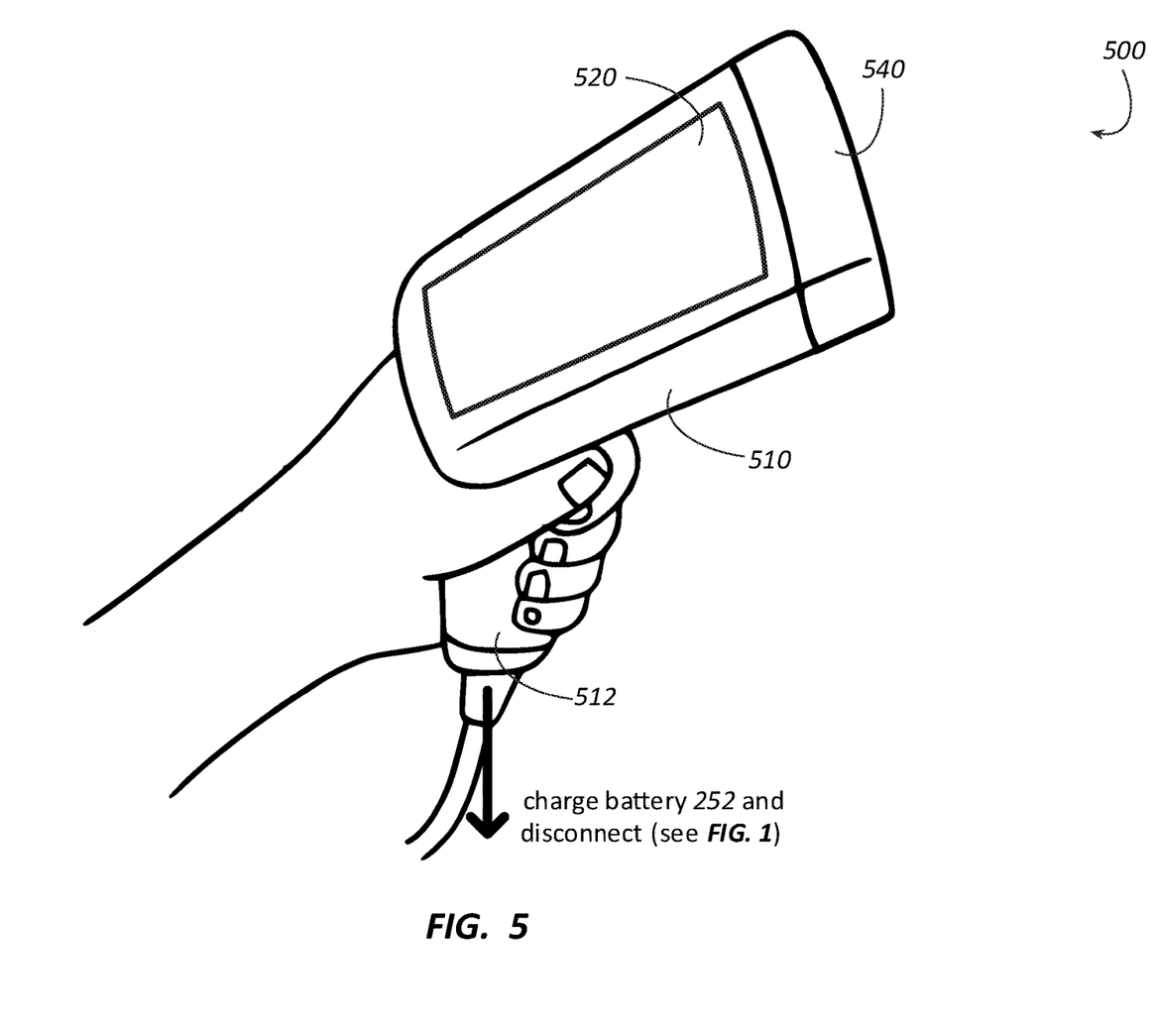
FIG. 5 illustrates an IPDD in accordance with some embodiments.

One or more portions of the implantable port 310 incorporate the contrast agent 317 for locating the septum 314 of the implantable port 310 in vivo by opto-electronic excitation and detection of the contrast agent 317 with the IPDD 500. The septum 314 of the implantable port 310 can incorporate the contrast agent 317 as shown in FIG. 3B.

Palpation bumps, of which three are shown in FIGS. 3B and 3C protruding from the septum 314, can incorporate the contrast agent 317. The housing 312 of the implantable port 310 can incorporate the contrast agent 317 around at least the major opening of the housing 312 as shown in FIG. 3C. The implantable port 310 including the contrast agent 317 is stable to conditions associated with autoclave-based sterilization up to a temperature of at least 60° C.

The contrast agent 317 can include nanoparticles, quantum dots, one or more fluorescent dyes, a combination thereof (e.g., fluorescently labeled nanoparticles), or a mixture thereof (e.g., nanoparticles and a fluorescent dye). For example, the contrast agent 317 can include nanoparticles. The nanoparticles can be of a type including up-converting nanoparticles including lanthanide- or actinide-doped transition metals. The nanoparticles can be of a type including core-shell nanoparticles including either an organic or inorganic core at least partially encased by at least one independently organic or inorganic shell. The nanoparticles can be of a type including gold nanoparticles or silver nanoparticles.

Figure 7:
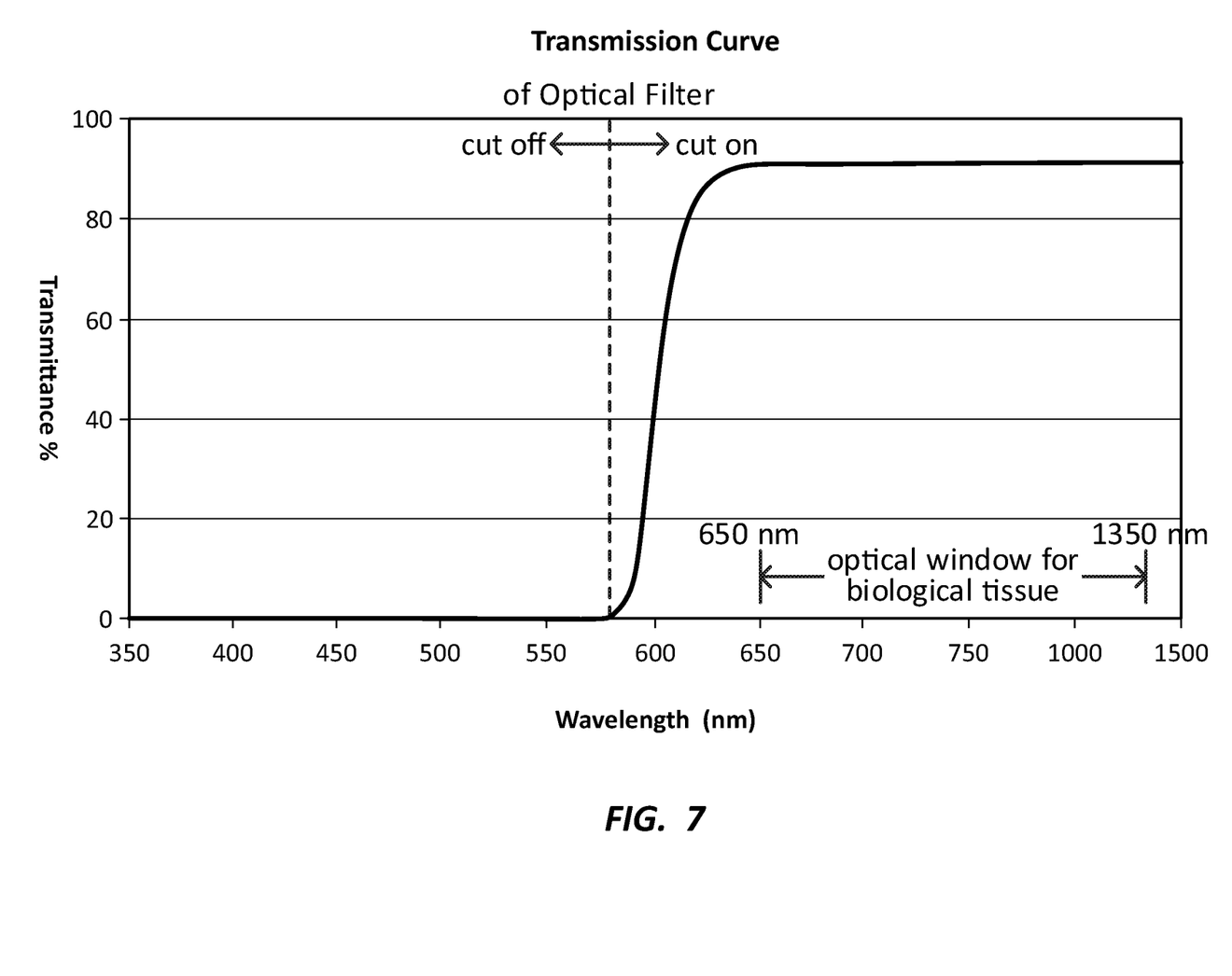
FIG. 7 illustrates a transmission curve for an optical filter of an IPDD in accordance with some embodiments.

The contrast agent 317 can be configured to absorb incident light at one or more wavelengths in an NIR range of wavelengths and emit luminescent light at one or more same or different wavelengths in the NIR range of wavelengths. The NIR range of wavelengths can be from about 650 nm to about 1350 nm, which is an optical window for biological tissue in that light in the foregoing range of wavelengths penetrates biological tissue more deeply than light outside the foregoing range of wavelengths. (See FIG. 7 for the optical window for biological tissue.)

The nanoparticles can be configured to absorb incident light and emit luminescent light by way of surface plasmon resonance in the optical window for biological tissue due to various shapes, sizes, or capping ligands of the nanoparticles. Depending upon a desired absorption of incident light and emission of luminescent light in the optical window for biological tissue, mixtures of two or more nanoparticles of different types (e.g., up-converting nanoparticles, core-shell nanoparticles, gold nanoparticles, silver nanoparticles) can be used to achieve the desired absorption of incident light and emission of luminescent light in the optical window for biological tissue. Alternatively, mixtures of two or more nanoparticles of a same type but having different shapes, sizes, or capping ligands can be used to achieve the desired absorption of incident light and emission of luminescent light in the optical window for biological tissue.

Figure 4A:
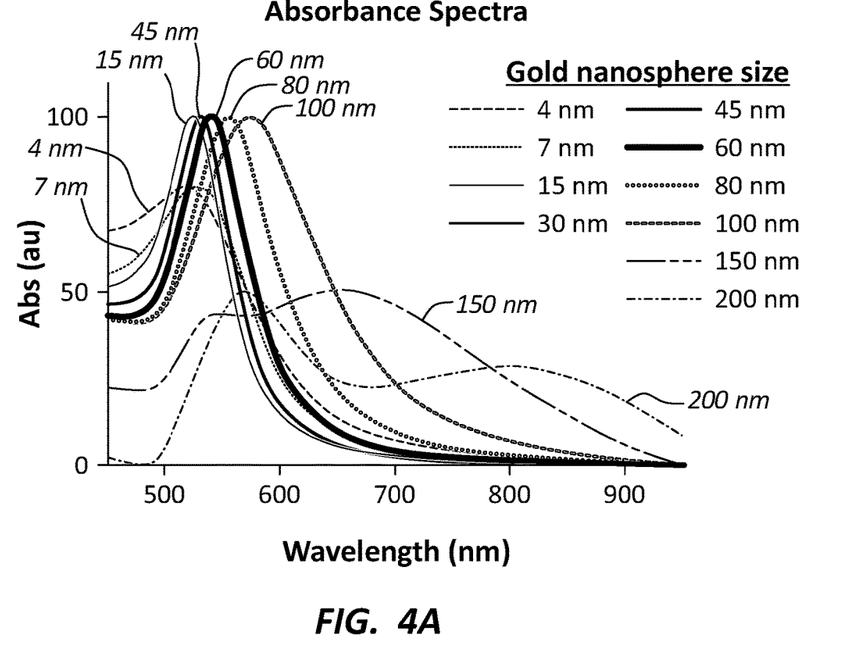
FIG. 4A illustrates absorbance spectra for gold nanospheres in accordance with some embodiments.
Figure 4B:
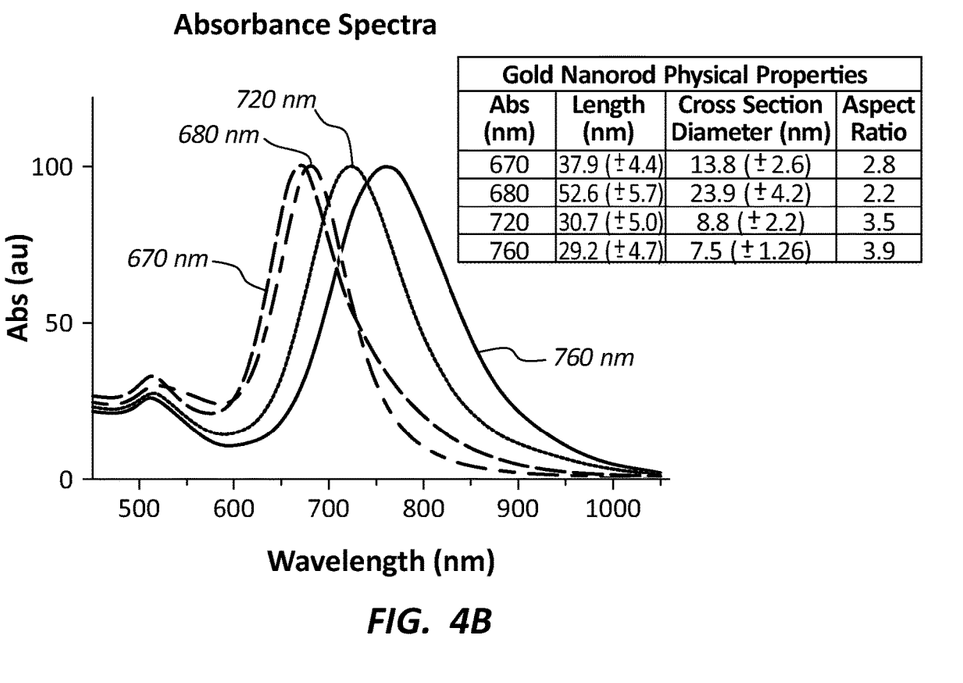
FIG. 4B illustrates absorbance spectra for gold nanorods in accordance with some embodiments.

The nanoparticles can be of various shapes, for example, at least gold nanoparticles can be gold nanospheres, gold nanorods, gold nanostars, or gold nanocups. The nanoparticles can be of various sizes, for example, at least gold nanospheres can be 4 nm, 7 nm, 15 nm, 30 nm, 45 nm, 60 nm, 80 nm, 100 nm, 150 nm, or 200 nm in diameter. Peak absorbance for each size of the foregoing gold nanospheres is between 520 nm to 850 nm (e.g., 520 to 580 nm for 15 to 100-nm gold nanospheres) and generally follows a trend in which the greater the diameter, the longer the wavelength of light absorbed at the peak absorbance. That said, the greater the diameter, the broader the peak absorbance until reaching the absorbance of the bulk metal (e.g., bulk gold in the case of gold nanoparticles). (See FIG. 4A for absorbance spectra of the foregoing gold nanospheres.) Gold nanorods can be 29.2 nm in length and 7.5 nm in diameter, 30.7 nm in length and 8.8 nm in diameter, 37.9 nm in length and 13.8 nm in diameter, or 52.6 nm in length and 23.9 nm in diameter respectively with an aspect ratio of 3.9, 3.5, 2.8, or 2.2. Peak absorbance for each size of the foregoing gold nanorods is between 570 nm to 760 nm. (See FIG. 4B for absorbance spectra of the foregoing gold nanospheres.)

With respect to capping ligands, for example, at least gold nanospheres or gold nanorods can include a capping ligand derived from biotin, methoxy polyethyleneglycol, or citric acid.

Implantable Port-Detecting Devices

Figure 6:
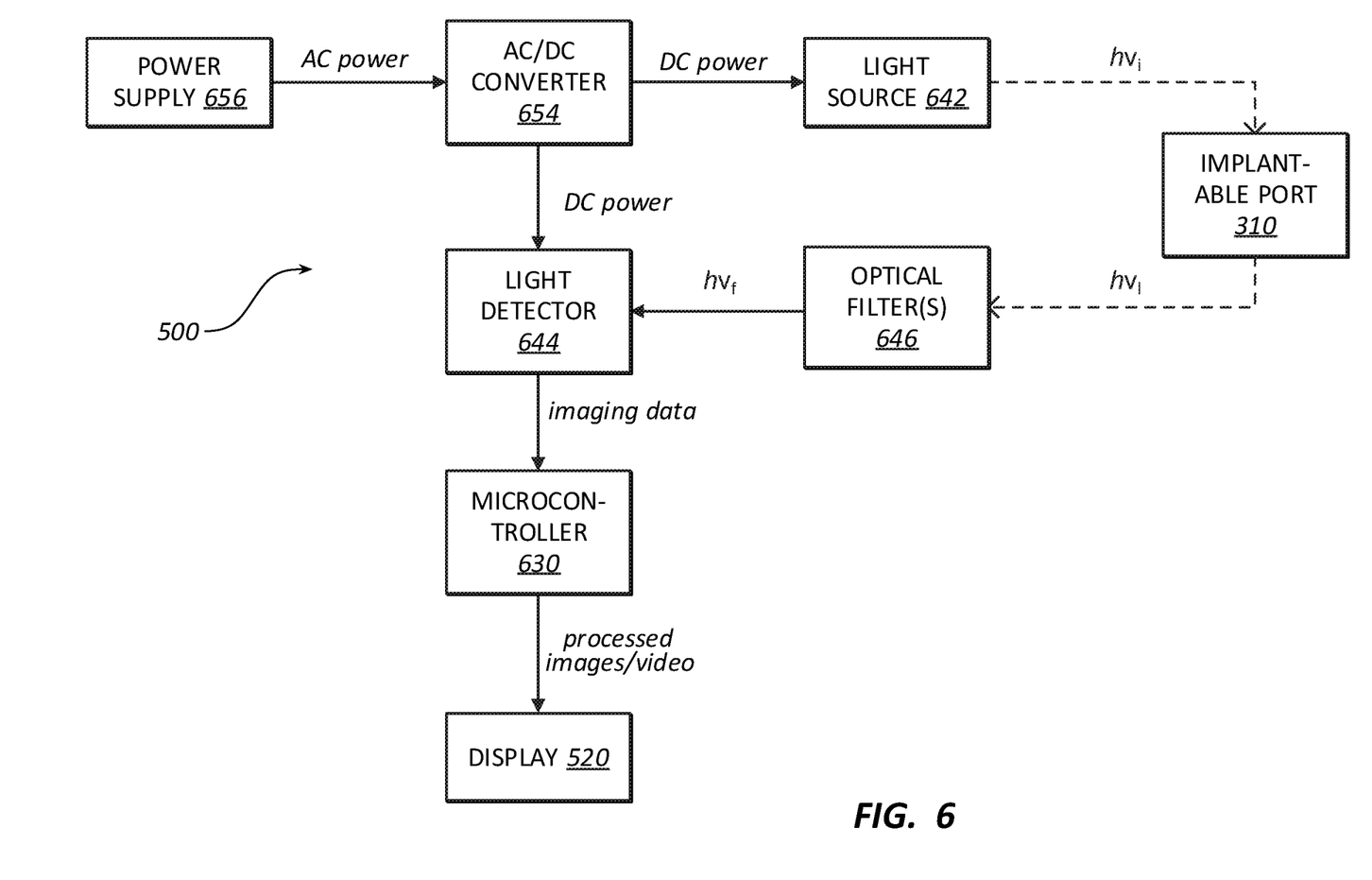
FIG. 6 illustrates modules of an IPDD in accordance with some embodiments.

FIG. 5 illustrates the IPDD 500 in accordance with some embodiments. FIG. 6 illustrates modules of the IPDD 500 in accordance with some embodiments.

As shown, the IPDD 500 includes, in some embodiments, a body 510 (e.g., a molded plastic body) including a handle 512 and the display 520 disposed in the body 510, thereby providing a handheld device. When the IPDD 500 is powered on, the display 520 is configured to provide a GUI 222 (see FIG. 2), which, in turn, is configured to display a presence of the implantable port 310 when the luminescent light from the contrast agent 317 is detected by the light detector 644. Disposed within at least a portion of the body 510, the IPDD 500 further includes a microcontroller 630 configured for at least operation of the IPDD 500 including image processing with an image-processing algorithm, a light sensor module 540, and a power system 250 (see FIG. 2) including a battery 252 (see FIG. 2) that can be charged by way of an AC/DC converter 654 configured to convert AC power (e.g., general-purpose AC electric power) from a power supply 656 to DC power for charging the battery 252.

The light sensor module 540 includes the light source 642, the light detector 644 (e.g., CCD sensor), and, optionally, one or more optical filters 646.

The light source 642 can be one or more lasers, LEDs, or a combination thereof configured to emit light of one or more wavelengths (e.g., 660 nm, 780 nm, 830 nm, 850 nm, or 860 nm) in the NIR range of wavelengths as the incident light $hv_i$ for absorption by the contrast agent 317 incorporated into the one or more portions of the implantable port 310. The incident light can be of one or more wavelengths at or near a peak absorbance of the contrast agent 317. When the contrast agent includes gold nanoparticles (e.g., gold nanospheres, gold nanorods, etc.), the incident light at or near the peak absorbance is thought to induce surface plasmon resonance, which, in turn, it thought to provide the luminescent light $hv_l$.

The light detector 644 is configured to detect light of one or more same or different wavelengths in the NIR range of wavelengths including the luminescent light emitted by the contrast agent 317 after the incident light is absorbed by the contrast agent 317. The light detector 644 can be an NIR-sensitive camera configured to capture images or video of at least a portion of an environment (e.g., a body surface of the patient P) together with the luminescent light from the contrast agent 317 of the implantable port 310 when the luminescent light is present. The display 520 can be configured to display the images or the video, thereby providing the presence of the implantable port 310 and the septum 314 thereof.

Because both the incident light from the light source 642 and the luminescent light emitted by the contrast agent 317 can be scattered by light-tissue interactions, the imaging algorithm can be configured, for example, with a peak contrast ratio finder, to automatically identify a so-called hotspot corresponding to the one or more wavelengths of luminescent light emitted by the contrast agent 317 of the implantable port 310. If the contrast agent 317 is incorporated in the septum 314, the imaging algorithm can be configured to identify a luminescent disk as the hotspot. If the contrast agent 317 is incorporated in the three palpation bumps protruding from the septum 314, the imaging algorithm can be configured to identify three luminescent spots as the hotspot. If the contrast agent 317 is incorporated in the housing 312 around the septum 314, the imaging algorithm can be configured to identify a luminescent annulus as the hotspot. When the light detector 644 is the NIR-sensitive camera, the hotspot—if not immediately identifiable in the image or video—can be identified by a graphical element in the GUI 222 when the images or video from the NIR-sensitive camera are displayed.

As an alternative or in addition to identifying the hotspot corresponding to the septum 314 of the implantable port 310 with the graphical element in the GUI 222 over the images or video from the NIR-sensitive camera, a laser can be used to identify the hotspot. The laser can be a laser of the one or more lasers of the light source 642 of the IPDD 500. If the laser is the same as that in use by any of the one or more lasers of the light source 642, the laser can be configured to alternately flash in at least two different wavelengths upon identifying the hotspot. A first wavelength in the NIR range of wavelengths can be flashed for continued excitation of the contrast agent 317, and a second wavelength can be flashed in a visible-light range of wavelengths for visual identification of the hotspot on the patient P. If the laser is different than that in use by any of the one or more lasers of the light source 642, the laser can be configured to solidly irradiate the hotspot in the visible-light range of wavelengths for visual identification of the hotspot on the patient P. The laser can also be configured to automatically point to and track the hotspot on the patient P when the IPDD 500 is being used. As such, the laser providing the visual identification of the hotspot on the patient P can be switched "on" when the septum 314 of the implantable port 310 is identified. Otherwise, the laser is switched off, thereby providing an easy mechanism for a clinician to identify the septum 314 of an implantable port 310 when implanted.

If the one or more optical filters 646 are used, the one or more optical filters 646 can be over an aperture of the light detector 644 such as over an aperture of the NIR-sensitive camera to cut off wavelengths of interfering light. In other words, the one or more optical filters 646 can be between the light detector 644 and the patient P. Thus, light from the portion of the environment (e.g., the body surface of the patient P) including the luminescent light from the contrast agent 317 of the implantable port 310 can be filtered by the one or more optical filters 646 to produce a filtered light $hv_f$, thereby cutting off the wavelengths of interfering light passed to the light detector 644. When the light detector 644 is the NIR-sensitive camera, cutting off the wavelengths of interfering light improves contrast in the images or the video produced. At least one optical filter of the one or more filters 646 can be a dichroic filter configured as a bandpass or longpass filter that cuts off wavelengths shorter than about 600 nm (i.e., both the ultraviolet and the visible portions of the electromagnetic spectrum having wavelengths greater than about 600 nm). (See FIG. 7 for a transmission curve of such an optical filter.)

Methods

A method of the implantable port-detection system 100 includes, in some embodiments, emitting light from the light source 642 of the IPDD 500 as incident light, detecting light with the light detector 644 of the IPDD 500 including luminescent light from the implantable port 310 implanted in the patient P, and displaying a presence of the implanted port 310 in the patient P. The incident light emitted from the light source 642 of the IPDD 500 is of one or more wavelengths in an NIR range of wavelengths. The luminescent light from the implantable port 310 is luminescent light emitted by the contrast agent 317 incorporated into the implantable port 310 after the incident light is absorbed by the contrast agent 317. The luminescent light is of one or more same or different wavelengths in the NIR range of wavelengths. Displaying the presence of the implanted port 310 in the patient P occurs when the luminescent light from the contrast agent 317 is detected by the light detector 644.

The light detector 644 can be an NIR-sensitive camera, and the method can further include capturing images or video. Displaying the presence of the implantable port 310 implanted in the patient P includes displaying the images or the video of at least a portion of a body surface of the patient P together with the luminescent light emitted by the contrast agent 317 incorporated into the implantable port 310 when the luminescent light is present.

The method can further include piercing the septum 314 of the implantable port 310 with a non-coring needle to collect a blood sample from the chamber 316 of the implantable port 310 or deliver a therapeutic agent to the chamber 316 of the implantable port 310. In addition, the method can further include removing the implantable port 310 implanted in the patient P.

Figure 8:
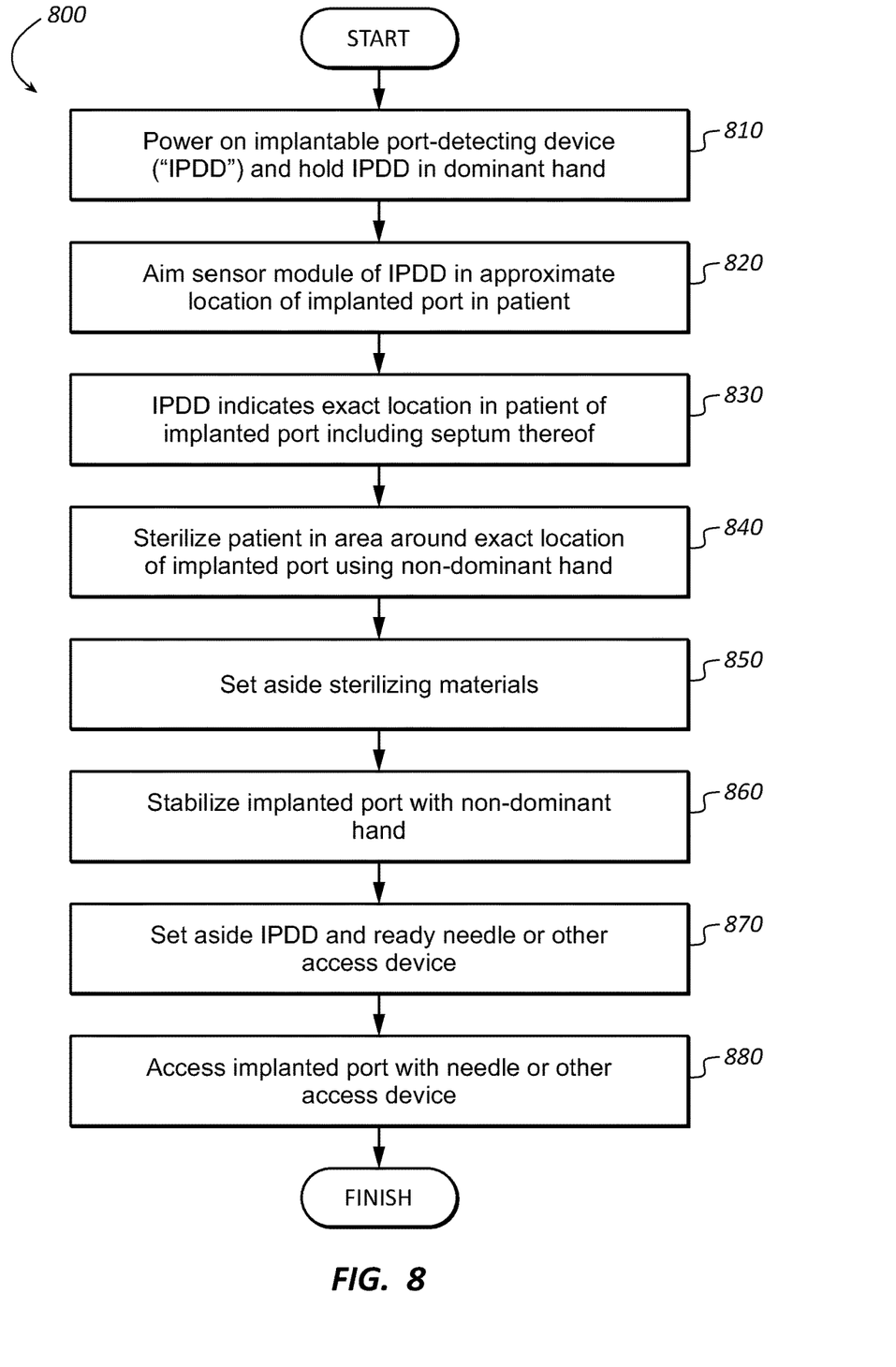
FIG. 8 illustrates a method of an implantable port-detection system in accordance with some embodiments.

FIG. 8 illustrates another method 800 of an implantable port-detection system 100 in accordance with some embodiments.

As shown, operation 810 includes powering on the IPDD 500 and holding the IPDD 500 in a dominant hand. Operation 820 includes aiming the sensor module 540 of the IPDD 500 in an approximate location of the implanted port in the patient P. Operation 830 includes the IPDD 500 indicating an exact location in the patient P of the implanted port including the septum 314 thereof. Operation 840 includes sterilizing the patient P in an area around the exact location of the implanted port using a non-dominant hand. Operation 850 includes setting aside materials used for sterilizing the patient P. Operation 860 includes stabilizing the implanted port with the non-dominant hand. Operation 870 includes setting aside the IPDD 500 and readying a needle or some other access device for access. Operation 880 includes accessing the implanted port with the needle or the other access device with the dominant hand.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An implantable port, comprising:
   a housing including a chamber having a major opening to the chamber; and
   a septum over the major opening of the housing, wherein:
      the implantable port incorporates a contrast agent in an annulus around the major opening of the housing for locating the septum of the implantable port in vivo by opto-electronic excitation and detection of the contrast agent, and
      the contrast agent including up-converting nanoparticles selected from lanthanide- and actinide-doped transition metals configured to absorb incident light at one or more wavelengths in the near-infrared ("NIR") range of wavelengths and emit luminescent light at one or more same or different wavelengths in the NIR range of wavelengths.

2. The implantable port of claim 1, wherein the implantable port including the contrast agent is stable to conditions associated with autoclave-based sterilization up to a temperature of at least 60° C.

3. The implantable port of claim 1, wherein the housing has a structural integrity for mechanically assisted pressurized injections to achieve a desired flow rate of injectant through the implantable port.

4. A catheter assembly, comprising:
   a) an implantable port including:
      a housing including a chamber having a major opening and a minor opening to the chamber;
      a septum over the major opening of the housing; and
      a stem including a stem lumen fluidly connected to the chamber by the minor opening of the housing, wherein:
         the implantable port incorporates a contrast agent in an annulus around the major opening of the housing for locating the septum of the implantable port in vivo by opto-electronic excitation and detection of the contrast agent, and
         the contrast agent including gold nanoparticles configured to absorb incident light at one or more wavelengths in the near-infrared ("NIR") range of wavelengths and emit luminescent light at one or more same or different wavelengths in the NIR range of wavelengths; and
   b) a catheter including an end portion configured to slide over the stem of the implantable port, the catheter having a catheter lumen in fluid communication with the chamber of the implantable port by way of the stem lumen; and
   c) a catheter lock configured to slide over the end portion of the catheter over the stem of the implantable port, thereby locking the catheter on the stem of the implantable port.

5. The catheter assembly of claim 4, wherein the gold nanoparticles include a capping ligand derived from biotin, methoxy polyethyleneglycol, or citric acid.

6. The catheter assembly of claim 4, wherein the implantable port including the contrast agent is stable to conditions associated with autoclave-based sterilization up to a temperature of at least 60° C.

7. The catheter assembly of claim 4, wherein the housing of the implantable port has a structural integrity for mechanically assisted pressurized injections to achieve a desired flow rate of injectant through the implantable port.

8. The catheter assembly of claim 4, wherein the gold nanoparticles are gold nanorods having an aspect ratio of about 3.9 and a corresponding peak absorbance of about 760 nm.

9. The catheter assembly of claim 4, wherein the gold nanoparticles are gold nanorods having an aspect ratio of about 3.5 and a corresponding peak absorbance of about 720 nm.

10. The catheter assembly of claim 4, wherein the gold nanoparticles are gold nanorods having an aspect ratio of about 2.2 or 2.8 and a corresponding peak absorbance of about 670 nm or 680 nm.

11. The catheter assembly of claim 4, wherein the gold nanoparticles are a mixture of two or more types of gold nanoparticles that differ with respect to shape, size, capping ligand, or some combination thereof to achieve a desired absorption of the incident light and emission of the luminescent light in the NIR range of wavelengths.

12. The catheter assembly of claim 11, wherein the shape of the gold nanoparticles is selected from gold nanospheres, gold nanorods, gold nanostars, and gold nanocups.

13. The catheter assembly of claim 12, wherein the size of the gold nanospheres is selected from 4 nm, 7 nm, 15 nm, 30 nm, 45 nm, 60 nm, 80 nm, 100 nm, 150 nm, and 200 nm in diameter, with greater diameters corresponding to greater wavelengths of light absorbed at peak absorbance.

14. The catheter assembly of claim 12, wherein the size of the gold nanorods is selected from 29.2 nm in length and 7.5 nm in diameter for an aspect ratio of 3.9, 30.7 nm in length and 8.8 nm in diameter for an aspect ratio of 3.5, 37.9 nm in length and 13.8 nm in diameter for an aspect ratio of 2.8, and 52.6 nm in length and 23.9 nm in diameter for an aspect ratio of 2.2.

15. The catheter assembly of claim 14, the gold nanorods having the aspect ratio of 3.9 having a corresponding peak absorbance of about 760 nm, the gold nanorods having the aspect ratio of 3.5 having the corresponding peak absorbance of about 720 nm, the gold nanorods having the aspect ratio of 2.2 having the corresponding peak absorbance of about 670 nm, and the gold nanorods having the aspect ratio of 2.8 having the corresponding peak absorbance of about 680 nm.

16. The catheter assembly of claim 4, wherein the contrast agent further includes up-converting nanoparticles selected from lanthanide- and actinide-doped transition metals to achieve a desired absorption of the incident light and emission of the luminescent light in the NIR range of wavelengths.

17. An implantable port-detection system, comprising:
   an implantable port including:
      a housing including a chamber having a major opening to the chamber; and
      a septum over the major opening of the housing, wherein:
         the implantable port incorporates a contrast agent in an annulus around the major opening of the housing for locating the septum of the implantable port in vivo by opto-electronic excitation and detection of the contrast agent; and
         the contrast agent including gold nanoparticles or up-converting nanoparticles selected from lanthanide- and actinide-doped transition metals configured to absorb incident light at one or more wavelengths in the near-infrared ("NIR") range of wavelengths and emit luminescent light at one or more same or different wavelengths in the NIR range of wavelengths; and
   an implantable port-detecting device ("IPDD"), comprising:
      a light source configured to emit light of one or more wavelengths in the NIR range of wavelengths as the incident light for absorption by the contrast agent incorporated into the implantable port;
      a light detector configured to detect the luminescent light emitted by the contrast agent after the incident light is absorbed by the contrast agent; and
      a display configured to display a presence of the implantable port when the luminescent light from the contrast agent is detected by the light detector.

18. The IPDD of claim 17, wherein the light detector is an NIR-sensitive camera configured to capture images or video of at least a portion of an environment including the implantable port together with the luminescent light from the contrast agent when the luminescent light is present.

19. The IPDD of claim 18, wherein the display is configured to display the images or the video, thereby providing the presence of the implantable port.

20. The IPDD of claim 18, further comprising an optical filter over an aperture of the NIR-sensitive camera configured to cut off wavelengths of interfering light to improve contrast in the images or the video.

21. The IPDD of claim 20, wherein the optical filter is a dichroic filter configured as a bandpass or longpass filter that cuts off wavelengths shorter than about 600 nm.

22. The IPDD of claim 17, further comprising a battery and a converter configured to convert alternating current ("AC") to direct current ("DC") for charging the battery by a general-purpose AC electric-power supply.

23. The IPDD of claim 17, wherein the IPDD is a handheld device.

* * * * *